United States Patent [19]

Allen et al.

[11] 4,447,547

[45] May 8, 1984

[54] IMMUNOASSAY FOR MEASUREMENT OF RETICULOCYTES, AND IMMUNOREACTIVE REAGENTS FOR USE THEREIN

[75] Inventors: Robert H. Allen, Englewood; Paul A. Seligman, Denver, both of Colo.

[73] Assignee: University Patents, Inc., Norwalk, Conn.

[21] Appl. No.: 356,539

[22] Filed: Mar. 9, 1982

Related U.S. Application Data

[62] Division of Ser. No. 138,785, Apr. 9, 1980, Pat. No. 4,332,785.

[51] Int. Cl.$^3$ .................... G01N 33/54; G01N 33/58; G01N 33/60
[52] U.S. Cl. .................................. 436/543; 436/544; 436/545; 436/546; 436/547
[58] Field of Search .................................. 424/1, 1.5; 436/543–547

[56] References Cited

U.S. PATENT DOCUMENTS

4,082,085  4/1978  Wardlaw et al. .................. 23/230 B
4,146,604  3/1979  Kleinerman ....................... 23/230 B
4,273,757  6/1981  Selhub et al. ........................... 424/1

OTHER PUBLICATIONS

Seligman et al., J. Biol. Chem., 254(1979): 9943–9946.
Trowbridge et al., Proc. Natl. Acad. Sci.: USA, 78(1981): 3039–3043.
Enns et al., Proc. Natl. Acad. Sci.: USA, 78(1981):4222–4225.
Trowbridge et al., Nature, 294(1981) 171–173.
Enns et al., J. Biol. Chem., 256(1981): 12620–12623.
Steiner, J. Lab. Clin. Med., 96(1980): 1086–1093.

*Primary Examiner*—Christine M. Nucker
*Attorney, Agent, or Firm*—George M. Yahwak

[57] ABSTRACT

The reticulocyte content present in a specimen of red blood cells is quantitatively measured based upon the selective immunoreactivity of the reticulocyte portion of the specimen with a reticulocyte-specific antibody which is immunoreactive with proteinaceous material associated with reticulocytes but not associated with mature red blood cells. Such immunoreactive proteinaceous material may be transferrin, transferrin receptor, transcobalamin II, or transcobalamin II receptor. Various procedures are described for quantitating such selective immunoreactivity, including fluorescent and radioactive detection techniques employing direct or indirect fluorescent or radioactive labeling of the reticulocyte-specific antibody.

4 Claims, No Drawings

IMMUNOASSAY FOR MEASUREMENT OF RETICULOCYTES, AND IMMUNOREACTIVE REAGENTS FOR USE THEREIN

BACKGROUND OF THE INVENTION

The invention described herein was made in the course of work under a grant or award from the Department of Health, Education and Welfare.

This application is a divisional of my prior application Ser. No. 138,785, filed on Apr. 9, 1980, now U.S. Pat. No. 4,332,785.

This invention relates to blood analysis and, more particularly, to the determination of the reticulocyte content present in a specimen of red blood cells.

Reticulocytes are newly synthesized red blood cells that have been released from the bone marrow within the preeceding twenty-four to forty-eight hours. In normal circulating blood, the reticulocyte count, i.e., the percentage of reticulocytes based upon the total number of red blood cells, is generally less than two percent.

Measurement of the reticulocyte count of a blood specimen is a highly useful diagnostic test, particularly in evaluating the cause of anemia in a patient. In patients with anemia, a high reticulocyte count indicates that the anemia is being caused by increased red cell loss, while a low reticulocyte count indicates the anemia being due to decreased red cell production. Also, increased reticulocyte counts found in patients with a normal hemoglobin and hematocrit may alert the physician to increased red cell loss.

The current methods which are commonly employed for determining reticulocyte counts utilize special stains which selectively stain nuclear remnants such as RNA which are found in reticulocytes but not in mature red blood cells. Following these time-consuming staining procedures, the reticulocytes are manually counted by using a microscope to determine the percentage of red blood cells that stain as reticulocytes.

The fact that reticulocytes contain RNA indicates that they are able to synthesize hemoglobin and other proteins. Previously performed binding studies have shown that iron bound to transferrin (the major iron transport protein in human plasma) and vitamin $B_{12}$ bound to transcobalamin II (the major vitamin $B_{12}$ transport protein in human plasma) are taken up by reticulocytes but not by mature red blood cells. This suggests that reticulocytes differ from mature red blood cells in containing receptors for transferrin and transcobalamin II, and, through such receptors, transferrin and transcobalamin II in bound form.

SUMMARY OF THE INVENTION

It is, accordingly, a primary object of the present invention to provide an improved method for determining reticulocyte counts which is more convenient and less time-consuming to carry out than existing, commonly employed procedures.

Another object of the invention is to provide a reticulocyte assay in accordance with the preceding object, which is readily adaptable for use in conjunction with automated counting techniques.

A further object of the invention is to provide a reticulocyte assay in accordance with the preceding objects, which is compatible for being carried out online in conjunction with standard techniques for determining total red blood cell count.

Still another object of the invention is to provide novel reagents which are capable of distinguishing reticulocytes from mature red blood cells with a high degree of specificity for use in carrying out the reticulocyte assay in accordance with the preceding objects.

The above and other objects are achieved in accordance with the present invention by means of an immunoassay procedure which takes advantage of the distinctiveness of reticulocytes from mature red blood cells in containing certain proteinaceous material, such as transferrin, transferrin receptor, transcobalamin II, and transcobalamin II receptor. The immunoassay employs as its primary reagent a reticulocyte-specific antibody which is substantially immunoreactive with the proteinaceous material substantially associated with reticulocytes but not substantially associated with mature red blood cells. In employing the immunoassay for quantitatively measuring the reticulocyte content present in a specimen of red blood cells, an incubation mixture is first formed comprising the specimen and the reticulocyte-specific antibody. The incubation mixture is then incubated for a period of time sufficient to enable immunoreaction to occur. This results in the reticulocyte-specific antibody forming an immunoreaction product selectivity with the reticulocyte portion of the specimen via the immunoreactive proteinaceous material. Thereafter, the reticulocyte portion of the specimen is quantitatively measured based upon the extent of the immunoreaction, which may be determined in any of several different ways. Particularly suitable as quantitating techniques are fluorescent or radioactive detection techniques employing direct or indirect fluoroescent or radioactive labeling of the reticulocyte-specific antibody.

The immunoassay of the present invention is readily adaptable for use in conjunction with standard manual or automated fluorescent or radioactive counting systems. Furthermore, the immunoassay together with its associated counting system is readily compatible with being carried out on-line in conjunction with standard techniques for determining total red blood cell count, thereby enabling an integrated system for determining both the total red blood cell count and the reticulocyte count of a blood specimen.

DESCRIPTION OF PREFERRED EMBODIMENTS

The reticulocyte-specific antibody employed as the primary reagent in the immunoassay of the present invention is defined as one which is substantially immunoreactive with proteinaceous material substantially associated with reticulocytes but not substantially associated with mature red blood cells. Such proteinaceous material is most suitably selected from the group consisting of transferrin, transferrin receptor, transcobalamin II, transcobalamin II receptor, and combinations thereof.

The antibody reagent may suitably be prepared by standard antibody-producing techniques in any suitable animal, most typically a rabbit, starting with a purified form of the proteinaceous material with which the antibody is to be immunoreactive. Purified human transferrin suitable for use in antibody production is commercially available, for example, from Sigma Chemical Company, St. Louis, Mo. Purified human transcobalamin II and purified human transcobalamin II receptor suitable for use in antibody production may suitably be prepared by the procedures described by Allen, et al., *J. Biol. Chem.*, Vol. 247, pp. 7709–7717 (1972) (Human transcobalamin II); and Seligman, et al., *J. Biol. Chem.*, Vol. 253, pp. 1766–1772 (1978) (Human transcobalamin II receptor), both of which are incorporated herein by reference.

A procedure for the preparation of purified human transferrin receptor, isolated from human placenta, and suitable for use in antibody production, has been developed by the present inventors. Such purification procedure, and the characterization of the purified human transferrin receptor obtained thereby, are described in detail in a published paper by Seligman, et al., appearing in *J. Biol. Chem.*, Vol. 254, No. 20, pp. 9943–9946 (Oct. 25, 1979), which paper is incorporated herein by reference. In carrying out such purification procedure, a crude solubilized transferrin receptor preparation is first obtained by mixing a human placental homogenate in physiologic buffer with approximately one percent Triton X-100, followed by centrifugation and recovery of the crude solubilized transferrin receptor preparation as the supernatant. This crude preparation also contains transferrin, both in free form and bound to the transferrin receptor. The transferrin receptor-transferrin complex is then precipitated from the crude preparation by mixing with ammonium sulfate, leaving the free transferrin measuring in the supernatant. The transferrin receptor-transferrin complex is then extracted from the ammonium sulfate precipitate with 0.1 percent Triton X-100 in physiologic buffer, and subjected to immunochromatography on an antihuman transferrin-Sepharose column, which binds the transferrin receptor-transferrin complex. The transferrin receptor substantially free of transferrin is then eluted from the immunochromatography column with an elution buffer composed of 20 mM glycine/NaOH, pH 10.0, 500 mM NaCl, and 0.5 percent Triton X-100. The transferrin receptor eluted from the immunochromatography column is then subjected to affinity chromatography on a human transferrin-Sepharose column, from which it is eluted with an elution buffer composed of 50 mM glycine/NaOH, pH 10.0, 1 M NaCl, and 1.0 percent Triton X-100. The transferrin receptor eluted from the affinity chromatography column is then concentrated by ammonium sulfate precipitation and extraction from the ammonium sulfate precipitate with 0.1 percent Triton X-100 in physiologic buffer, to form the final purified transferrin receptor preparation. This purification procedure results in the isolation of human transferrin receptor having a purity of greater than 95 percent from a human placental starting material containing the transferrin receptor in a concentration of less than 0.01 percent.

Preparation of the antibody reagent from the purified proteinaceous material may be carried out by standard techniques well known in the art, i.e., by injection of any suitable animal, such as rabbits, goats, sheep, etc., with the purified proteinaceous material, and subsequent collection of the resulting antiserum. In a typical procedure, an injectable preparation of the purified proteinaceous material is prepared in physiologic buffer mixed with an equal volume of Freund's complete adjuvant. Rabbits are injected with this preparation, each rabbit receiving 100 $\mu$g of the proteinaceous material on Day 1, given as injections of 25 $\mu$g into each foot pad. The rabbits are boosted on Day 30 by injections given in the same manner, except that the amount of proteinaceous material injected per rabbit is reduced to 40 $\mu$g. The rabbits are bled on Day 40. The blood is allowed to clot at room temperature for one hour, and then stored at 4° C. for sixteen hours. The antisera are then collected by centrifugation, e.g., at 20,000×g for thirty minutes, and stored at $-20°$ C. Monoclonal antibodies may also be prepared using a technique such as mouse hydridomas.

For use as the antibody reagent in carrying out the immunoassay of the present invention, the antisera obtained in the above manner may suitably be employed as such. Alternatively, purified antibody can be obtained from the antisera by conventional means, for example, ammonium sulfate precipitation or affinity chromatography on antigen-Sepharose, and the antibody in thus-purified form may be employed as the antibody reagent.

The form of the specimen of red blood cells whose reticulocyte count is being measured depends upon the particular reticulocyte-specific antibody reagent being employed. Blood serum normally contains a significant amount of free, unbound transferrin and transcobalamin II. Due to this fact, when the antibody reagent is anti-transferrin antibody or anti-transcobalamin II antibody, the red blood cells must be separated from the blood serum, washed with physiologic buffer (e.g., phosphate-buffered saline or 10 mM potassium phosphate, pH 7.5, 150 mM NaCl), and then resuspended in physiologic buffer. On the other hand, when the antibody reagent is anti-transferrin receptor antibody or anti-transcobalamin II receptor antibody, the red blood cells need not be washed and can be subjected to the immunoassay in blood serum suspension form. For this reason, coupled with its higher sensitivity with respect to reticulocytes in comparison with anti-transcobalamin II receptor antibody, the preferred antibody reagent for use in the immunoassay of the present invention is anti-transferrin receptor antibody.

In carrying out the immunoassay in accordance with the present invention, an incubation mixture is first formed comprising the specimen of red blood cells whose reticulocyte content is to be measured, and the reticulocyte-specific antibody reagent. The relative proportions of these components of the incubation mixture may vary over a rather broad range. In general, with an incubation mixture containing approximately $2 \times 10^8$ red blood cells, the antibody reagent should be employed in an amount providing, broadly, from about 0.0001 to about 100, and preferably, from about 0.1 to about 10 $\mu$g of the reticulocyte-specific antibody. As a general rule, the reticulocyte-specific antibody concentration in the antisera as collected from the animal will be approximately 1 $\mu$g/$\mu$l. Thus, when the antisera is used directly as the antibody reagent without further antibody purification, from about 0.0001 to aout 100 $\mu$l of the antisera will provide the requisite amount of reticulocyte-specific antibody. If desired, the antisera can be diluted with physiologic buffer to a volume which is most convenient for use in forming the incubation mixture. For example, a suitable incubation mixture may conveniently be formed by adding to 50 $\mu$l of red blood cell suspension the requisite amount of reticulocyte-specific antibody in a volume of 10 to 100 $\mu$l.

The thus-formed incubation mixture is then incubated for a period of time sufficient to enable immunoreaction to occur. The requisite time period will vary, depending upon the temperature at which the incubation is carried out, with lower incubation temperatures requiring longer incubation periods. In general, the incubation period may vary from about five minutes to about twelve hours at incubation temperatures within the range of from about 4° to about 37° C. Particularly suitable incubation schedules are thirty minutes at 37° C. or two hours at room temperature.

The immunoassay of the present invention is based upon the selective immunoreactivity of the reticulocyte portion of the red blood cell specimen with the reticulocyte-specific antibody reagent via the immunoreactive proteinaceous material which is substantially associated with the reticulocytes but not substantially associated with the mature red blood cells. Quantitating such selective immunoreactivity based upon the extent of the immunoreaction serves as a quantitative measurement of the reticulocyte portion of the specimen. Any one of several different quantitating techniques may be employed in conjunction with the immunoassay for making such quantitative measurement.

The quantitating technique employed with the immunoassay of the present invention may be based upon the amount of the immunoreaction product formed between the reticulocyte portion of the red blood cell specimen and the reticulotye-specific antibody reagent. This may be determined as the amount of bound antibody present in the immunoreaction product, which may be quantitated by standard manual or automated fluorescent or radioactive detection techniques well known in the art employing direct or indirect fluorescent or radioactive labeling of the reticulocyte-specific antibody. Thus, the reticulocyte-specific antibody when incorporated into the incubation mixture may be in fluorescent-labeled form, labeled with a suitable fluorescent labeling agent such as, for example, fluorescein or rhodamine, or it may be in radioactive-labeled form, labeled with a suitable radioactive labeling agent such as, for example, $^{125}I$ or $^{131}I$.

Alternatively, the reticulocyte-specific antibody when incorporated into the incubation mixture may be in unlabeled form, and labeling may be effected subsequent to the immunoreaction by incubating the immunoreaction product with a fluorescent-labeled or radioactive-labeled substance which is bindable to the immunoreacted reticulocyte-specific antibody. Such antibody-bindable substance will typically be a second antibody directed against the reticulocyte-specific antibody, i.e., raised to the globulins of the animal source of the reticulocyte-specific antibody (anti-IgG). Alternatively, the antibody-bindable substance may be, for example, Staphylococcal A protein, a protein which is known to bind to antibodies.

With either the direct or indirect fluorescent or radioactive labeling approach described above, the fluorescence or radioactivity, as the case may be, exhibited by the immunoreaction product may be quantitated by standard manual or automated fluorescent or radioactive counting techniques well known in the art, thereby providing a quantitative measurement of the reticulocyte content of the red blood cell specimen.

Another technique for determining the amount of the immunoreaction product formed between the reticulocyte-specific antibody and the reticulocyte portion of the red blood cell suspension, involves the use of complement to the reticulocyte-specific antibody. Such complement may be added to the incubation mixture, and the amount of the immunoreaction product formed may then be determined by measurement of the resulting complement-mediated effects. For example, this procedure might result in swelling of the reticulocytes, thus allowing for differentiation from mature red blood cells by size. Also, this procedure might cause complete complement-mediated hemolysis of the reticulocytes, which could be quantitated in an automated system by measuring the amount of hemoglobin released or by the loss of a subpopulation of larger sized cells noted before the cells are treated.

The quantitative measurement of the reticulocyte portion of the specimen may also be based upon the amount of the immunoreactive proteinaceous material present in the specimen. For carrying out the immunoassay of the present invention in this manner, the incubation mixture will also contain a known amount of the immunoreactive proteinaceous material in addition to that present in the specimen and in radioactive-labeled form, and the amount of the immunoreactive proteinaceous material present in the specimen will be determined by standard radioimmunoassay techniques well known in the art.

The immunoassay of the present invention, particularly when employed in conjunction with the fluorescent or radioactive detection techniques described above, can be readily adapted to an automated system for reticulocyte counting by adding the appropriate reticulocyte-specific antibody to a blood cell specimen subjected to an existing flow system used for cell counting. All red blood cells would be counted in the flow system, and a fluorescent or radioactive detector could be situated online down stream from the cell counter. Then, using existing computerized techniques, the number of fluorescent or radioactive cells could be tabulated, and the percentage of reticulocytes quantitated.

The invention is further illustrated by way of the following examples.

EXAMPLE 1

This example illustrates the preparation of purified human transferrin receptor, isolated from human placenta.

A placental homogenate was prepared by cutting two placentas weighing a total of 1500 g into approximately 40 g pieces, and homogenizing them in a Waring Blendor for 30 seconds in 1.5 volumes of 10 mM $KPO_4$, pH 7.5, containing 150 mM NaCl. The mixture was centrifuged, and the pellets were resuspended in 1500 ml of the same buffer and frozen. The frozen homogenate could be stored for up to 3 days with no loss of receptor activity.

The resuspended pellet was thawed and 500 ml of 10 mM $KPO_4$, pH 7.5, containing 150 mM NaCl and 4 percent Triton X-100 was added. Solubilization was then continued utilizing homogenization with a Waring Blendor, sonication, and centrifugation. Crude solubilized transferrin receptor preparation was recovered as the supernatant.

Solid ammonium sulfate, 31.5 g/100 ml, was added to the supernatant from the previous step. After stirring for 10 minutes at 4° C., the sample was centrifuged at 20,000×g for 20 minutes at 4° C. Since the Triton X-100 present caused flotation of the precipitate, clear centrifuge bottles were used, and the supernatant was aspirated with a vacuum suction device. The precipitate was resuspended in 600 ml of 10 mM $KPO_4$, pH 7.5, containing 150 mM NaCl and 0.1 percent Triton X-100 and dialyzed against 4 liters of the same solution for 16 hours. The dialysate was changed at 4 and 12 hours.

The dialyzed ammonium sulfate preparation from the previous step was centrifuged in 200-ml portions at 16,000×g for 20 minutes. The supernatant was then applied to a column (2×30 cm) containing 60 ml of antihuman transferrin-Sepharose equilibrated in 10 mM KPO$_4$, pH 7.5, 150 mM NaCl (equilibration buffer), and 0.1% Triton X-100 at 4° C. It was necessary to centrifuge the dialyzed ammonium sulfate preparation just before applying it to the column to prevent the slow formation of precipitates which would not allow the flow rate of 50 ml/h to be maintained. After 200 ml of solution had been applied, the column was washed with a variety of solutions in the following order: wash (1) 200 ml of equilibration buffer; wash (2) 100 ml of 10 mM KPO$_4$, pH 7.5, 500 mM NaCl; wash (3) 100 ml of equilibration buffer; wash (4) 200 ml of 20 mM glycine/NaOH, pH 10.0, 500 mM NaCl, and 0.5% Triton X-100; and wash (5) 100 ml of 10 mM glycine/HCl, pH 2, 150 mM NaCl. The flow rate for washes 1 to 3 was 100 ml/h and 50 ml/h for washes 4 and 5. Wash 4 contained the bulk of the receptor activity. Wash 5 was performed to remove all the bound transferrin so the affinity column could be reused. Solid ammonium sulfate (31.5 g/100 ml) was added to wash 4, and the solution was stirred and centrifuged, the supernatant was aspirated, and the pellet was resuspended in 100 ml of equilibration buffer and dialyzed as described above in the previous ammonium sulfate precipitation step.

The dialyzed ammonium sulfate pellet from the previous step was applied to a column (1.5×15 cm) containing 15 ml of human transferrin-Sepharose in equilibration buffer. The column was then washed with the following solutions: wash (1) 100 ml of equilibration buffer; wash (2) 40 ml of 10 mM KPO$_4$, pH 7.5, 1 M NaCl; wash (3) 20 ml of equilibration buffer; and wash (4) 40 ml of 50 mM glycine/NaOH, pH 10.0, 1 M NaCl, and 1.0% Triton X-100. Wash 4, which contained the bulk of receptor activity, was concentrated to 4 ml using ammonium sulfate precipitation, and dialyzed against equilibration buffer as described above in the previous ammonium sulfate precipitation steps, to obtain the final transferrin receptor preparation.

The final transferrin receptor preparation contained 1.2 mg of protein. Assays for immunoreactive transferrin indicated that the preparation contained only 15 μg of transferrin which could be removed by passing the solution over an antihuman transferrin-Sepharose column.

The final transferrin receptor preparation gave a single band on polyacrylamide disc gel electrophoresis which coincided with a single peak of $^{125}$I-transferrin binding ability, and stained for both protein and carbohydrate. On sodium dodecyl sulfate-polyacrylamide gel electrophoresis, the transferrin receptor had a molecular weight of 150,000, and dissociated into 90,000, 60,000 and 30,000 molecular weight components after reduction with 2-mercaptoethanol.

EXAMPLE 2

This example illustrates the preparation in rabbits of anti-human transferrin receptor antibody from the purified human transferrin receptor prepared in Example 1.

The purified human transferrin receptor preparation as prepared in Example 1, in physiologic buffer, was mixed with an equal volume of Freund's complete adjuvant. Each rabbit received 1 ml of this mixture, containing 100 μg of transferrin receptor, on Day 1, given as injections of 0.25 ml into each footpad. Rabbits were boosted on Day 30 by injections given in the same manner, except that the amount of transferrin receptor injected per rabbit was reduced to 40 μg. Rabbits were bled on Day 40. The blood was allowed to clot at room temperature for 1 hour, and then was stored at 4° C. for 16 hours. The antisera were then collected by centrifugation at 20,000×g for 30 minutes and stored at −20° C.

The thus prepared anti-human transferrin receptor antibody was found to inhibit the binding of $^{125}$I-transferrin to purified human transferrin receptor. The antibody gave a single precipitin line against the purified transferrin receptor which cross-reacted with a pattern of identity with solubilized placental homogenate and solubilized red cell membranes from a patient with a 20 percent reticulocyte count; no precipitin line was seen with solubilized red cells from a subject with less than 2 percent reticulocytes. This information indicates that the transferrin binding protein that was isolated is the placental cell surface transferrin receptor and shows that the placental transferrin receptor is immunologically related to the transferrin receptor on the reticulocyte membrane. The data also suggests that immunoreactive reticulocyte transferrin receptor is altered or lost from the cell surface as the reticulocyte matures into a normal red cell.

EXAMPLE 3

This example illustrates the reticulocyte immunoassay of the present invention, carried out as a double antibody immunofluorescent technique.

A specimen of red blood cells (2×10$^8$) known to have a 20 percent reticulocyte count was washed in physiologic buffer (10 mM KPO$_4$, pH 7.5, 150 mM NaCl), then suspended in 50 μl of the physiologic buffer, and then incubated with 10 μl of the rabbit anti-human transferrin receptor antisera prepared as in Example 2, above. The incubation was carried out for 30 minutes at 37° C. The cells were again washed in physiologic buffer, resuspended in 50 μl of the physiologic buffer, and reincubated with 100 μl of the second antibody, which was fluorescein-labelled goat anti-rabbit globulin, for 30 minutes at 37° C. After a final wash in physiologic buffer, the cells were examined under microscopy using both a phase and fluorescent light source. The phase field showed a clump of reticulocytes surrounded by mature red blood cells. The same field using the fluorescent source showed that only the reticulocytes exhibited membrane fluorescence, whereas the mature red blood cells did not. The fluorescence was not quenched when endogenous transferrin was stripped from the reticulocytes, or when the antisera was previously absorbed with excess transferrin.

The above procedure was repeated, but this time employing as the first antibody rabbit anti-human transferrin antisera. Again, the comparison between the phase source and the fluorescent source showed that the reticulocytes exhibited membrane fluorescence, whereas the mature red blood cells did not. This time, however, the fluorescence was quenched when endogenous transferrin was stripped from the reticulocytes, or when the antisera was previously absorbed with excess transferrin.

EXAMPLE 4

The double antibody immunofluorescent technique as described in Example 3, above, was used for determining the reticulocyte counts of blood specimens obtained from a patient having pernicious anemia diagnosed by low serum B$_{12}$ and an abnormal Schilling test.

With patients of this type, an injection of vitamin $B_{12}$ results in a dialy increase in reticulocyte count, with peak reticulocyte response expected 4 to 5 days following the injection. The patient was given his first injection of vitamin $B_{12}$ on Day 1. Reticulocyte counts were measured on the day preceding the injection (Day 0) and daily for the 4 days subsequent to the injection (Days 2 to 5). Reticulocyte counts employing the double antibody immunofluorescent technique of the present invention were determined as the percent fluoroescent cells based upon the counting of 1,000 red blood cells. The reticulocyte counts were the same employing either anti-human transferrin receptor antisera or anti-human transferrin antisera as the first antibody in the double antibody immunofluorescent technique. For purposes of comparison, simultaneous reticulocyte counts were also performed using standard supravital staining techniques and also counting 1,000 red blood cells. The resulting reticulocyte counts obtained are set forth in Table I, below, which also lists for comparison purposes reticulocyte counts performed on a normal subject.

TABLE I

| Day | Reticulocyte Count | |
| --- | --- | --- |
| | Immunofluorescent Technique | Supravital Stain Technique |
| 0 | 0.5 | 1.7 |
| 2 | 2.0 | 5.0 |
| 3 | 6.0 | 9.0 |
| 4 | 15.0 | 19.0 |
| 5 | 16.0 | 22.0 |
| Normal | 0.2 | 0.8 |

It can be seen from Table I, that reticulocyte counts employing the immunofluorescent technique in accordance with the present invention are somewhat lower than those obtained using the standard supravital staining technique, although the results are still comparable. It is likely that with a more sensitive fluorescent detector, reticulocyte counts using the immunofluorescent technique would be the same as with the standard survival staining method.

When the double antibody immunofluorescent technique described above was carried out employing as the first antibody either anti-human transcobalamin II antibody or anti-human transcobalamin II receptor antibody, the results were comparable, but with much lower levels of fluorescence being observed on the reticulocytes. Again, it is likely that an improved level of fluorescence would be obtained utilizing a more sensitive fluorescent detector.

The embodiments of the invention in which an exclusive property or privilege is claimed are defined as follows:

1. Anti-human transferrin receptor antibody.
2. The antibody of claim 1, in fluorescent-labeled form.
3. The antibody of claim 1, in radioactive-labeled form.
4. Purified human transferrin receptor.

* * * * *

UNITED STATES PATENT AND TRADEMARK OFFICE
CERTIFICATE OF CORRECTION

PATENT NO. : 4,447,547

DATED : May 8, 1984

INVENTOR(S) : Robert H. Allen & Paul A. Seligman

It is certified that error appears in the above—identified patent and that said Letters Patent is hereby corrected as shown below:

Column 10, Lines 16 & 17, "survival" should read --supravital--

Signed and Sealed this

Twenty-first Day of August 1984

[SEAL]

Attest:

GERALD J. MOSSINGHOFF

Attesting Officer

Commissioner of Patents and Trademarks